US009901365B1

(12) United States Patent
Rosenhan (10) Patent No.: US 9,901,365 B1
(45) Date of Patent: Feb. 27, 2018

(54) SET OF SAFETY SCALPELS

(71) Applicant: PenBlade, Inc., Salt Lake City, UT (US)

(72) Inventor: Branden D. Rosenhan, Salt Lake City, UT (US)

(73) Assignee: PENBLADE, INC., Salt Lake City, UT (US)

( * ) Notice: Subject to any disclaimer, the term of this patent is extended or adjusted under 35 U.S.C. 154(b) by 608 days.

(21) Appl. No.: 14/216,483

(22) Filed: Mar. 17, 2014

Related U.S. Application Data (60) Provisional application No. 61/801,989, filed on Mar. 15, 2013.

(51) Int. Cl.
*A61B 17/3211* (2006.01)
*A61B 17/04* (2006.01)

(52) U.S. Cl.
CPC ...... *A61B 17/3211* (2013.01); *A61B 17/0467* (2013.01); *A61B 2017/32113* (2013.01)

(58) Field of Classification Search
CPC .................. A61B 2017/32113; A61B 17/3211
USPC .................................... 30/151–162; D24/147
See application file for complete search history.

(56) References Cited

U.S. PATENT DOCUMENTS

| 117,588 | A | 8/1871 | Woods |
| 256,629 | A | 4/1882 | Boman |
| 3,484,940 | A | 12/1969 | Zell |
| 3,699,654 | A | 10/1972 | Gerling |
| 3,945,117 | A * | 3/1976 | Beaver .............. A61B 17/32093 606/172 |
| 4,242,795 | A | 1/1981 | Rollband et al. |
| 4,423,729 | A | 1/1984 | Gray |
| 5,015,252 | A | 5/1991 | Jones |
| 5,250,064 | A * | 10/1993 | Schneider .......... A61B 17/3211 606/167 |
| 5,330,494 | A * | 7/1994 | van der Westhuizen ........................ A61B 17/3211 30/151 |
| 5,478,346 | A * | 12/1995 | Capewell ................ B26B 29/02 30/151 |
| 5,522,828 | A * | 6/1996 | Malilay .............. A61B 17/3211 30/153 |
| 5,630,242 | A | 5/1997 | Oginaezawa |

(Continued)

FOREIGN PATENT DOCUMENTS

| DE | 4240532 | 3/1994 |
| KR | 1020070095619 | 10/2007 |

OTHER PUBLICATIONS

International Preliminary Report on Patentability and Written Opinion of PCT/US2011/066191, dated Sep. 14, 2012.

*Primary Examiner* — Jason Daniel Prone
(74) *Attorney, Agent, or Firm* — Workman Nydegger (57) ABSTRACT

A set of safety scalpels includes a first subset having a first sized scalpel blade and a second subset having a second sized scalpel blade. The first sized scalpel blade shaped differently than the second. Each of the plurality of safety scalpels includes an identical safety scalpel support structure and a sheath configured to be coupled to the support structure to move between a safe position and an exposed position. The sheath has a transverse slot suitable for cutting suture and intersects the cutting edge of the first and second sized scalpel blade, respectively, when assembled therewith and in the safe position.

14 Claims, 8 Drawing Sheets

(56) References Cited

U.S. PATENT DOCUMENTS

| | | | |
|---|---|---|---|
| 5,676,677 A * | 10/1997 | Landis | A61B 17/3211 30/162 |
| 5,860,993 A | 1/1999 | Thompson et al. | |
| 5,868,771 A * | 2/1999 | Herbert | A61B 17/3213 30/162 |
| 5,919,201 A | 7/1999 | Carter et al. | |
| 6,254,620 B1 | 7/2001 | Koh et al. | |
| 6,446,340 B1 | 9/2002 | Ping | |
| D470,587 S * | 2/2003 | Howell | D24/147 |
| D470,938 S * | 2/2003 | Howell | D24/147 |
| D473,649 S * | 4/2003 | Howell | D24/146 |
| D475,135 S * | 5/2003 | Howell | D24/147 |
| 6,938,345 B2 | 9/2005 | Yu | |
| D535,026 S * | 1/2007 | Griffin | D24/146 |
| D561,898 S * | 2/2008 | Goto | D24/146 |
| 7,810,241 B2 * | 10/2010 | Pooler | A61B 17/3211 606/167 |
| D633,616 S * | 3/2011 | Lafauci | D24/147 |
| 8,167,897 B2 * | 5/2012 | Muto | A61B 17/3211 606/167 |
| 8,181,352 B1 | 5/2012 | Shackelford | |
| 8,291,601 B2 * | 10/2012 | Kehr | A61B 17/3213 606/167 |
| 8,465,512 B2 * | 6/2013 | Rosenhan | A61B 17/0467 606/167 |
| 8,959,778 B2 * | 2/2015 | Baid | A61B 17/3213 30/151 |
| 9,072,512 B2 * | 7/2015 | Rosenhan | A61B 17/0467 606/167 |
| 9,421,031 B2 * | 8/2016 | Morgan | A61B 17/3213 606/167 |
| 2002/0143352 A1 | 10/2002 | Newman et al. | |
| 2003/0074013 A1 * | 4/2003 | Schooler | A61B 17/3213 606/167 |
| 2004/0087989 A1 * | 5/2004 | Brenneman | A61B 17/3213 606/167 |
| 2004/0236359 A1 | 11/2004 | Shi | |
| 2004/0254598 A1 | 12/2004 | Schumacher et al. | |
| 2005/0150115 A1 | 7/2005 | Hanna | |
| 2005/0234481 A1 | 10/2005 | Waller | |
| 2006/0241665 A1 | 10/2006 | Bosley et al. | |
| 2008/0271323 A1 | 11/2008 | Perlmutter | |
| 2009/0131963 A1 * | 5/2009 | Rasco | A61B 17/3213 606/172 |
| 2009/0157110 A1 | 6/2009 | Muto et al. | |
| 2010/0125289 A1 * | 5/2010 | Kehr | A61B 17/3213 606/167 |
| 2010/0234865 A1 | 9/2010 | Lafauci et al. | |
| 2012/0165836 A1 * | 6/2012 | Rosenhan | A61B 17/0467 606/138 |
| 2012/0259352 A1 | 10/2012 | Rosenhan | |
| 2014/0182140 A1 * | 7/2014 | Rosenhan | B26B 5/003 30/162 |
| 2015/0282831 A1 * | 10/2015 | Jesseph et al. | A61B 17/3211 606/167 |

* cited by examiner

SET OF SAFETY SCALPELS

CROSS REFERENCE TO RELATED APPLICATIONS

This Application claims the benefit of U.S. Provisional Patent Application No. 61/801,989, filed Mar. 15, 2013, which is hereby incorporated by reference in its entirety.

BACKGROUND

Field of Use

The present invention relates to cutting devices such as safety scalpels and safety cutting devices.

Related Technology

Medical practitioners often close a wound or opening within a patient (e.g., during surgery) using sutures. Scalpels are often used as needed in performing the surgery, and then are often used for cutting the ends of sutures employed to close up the wound or opening within the patient's tissue. Depending on the nature of the procedure, sutures can be placed adjacent to a main artery or vein, and as such, any misplacement of the scalpel when cutting the suture (e.g., caused by an accidental sneeze, cough, or otherwise) could result in harm to the patient. As an alternative, it is possible to cut the sutures with scissors, but this requires a separate tool, which can be something of a nuisance to the practitioner, as the practitioner already has a scalpel handy.

Many scalpels include a safety sheath that covers the blade end of the scalpel. In order to use the blade (e.g., for cutting tissue or a suture) the sheath must be retracted or removed, or a retractable blade must be extended beyond the sheath, so as to expose the blade for use.

Figure 1A:
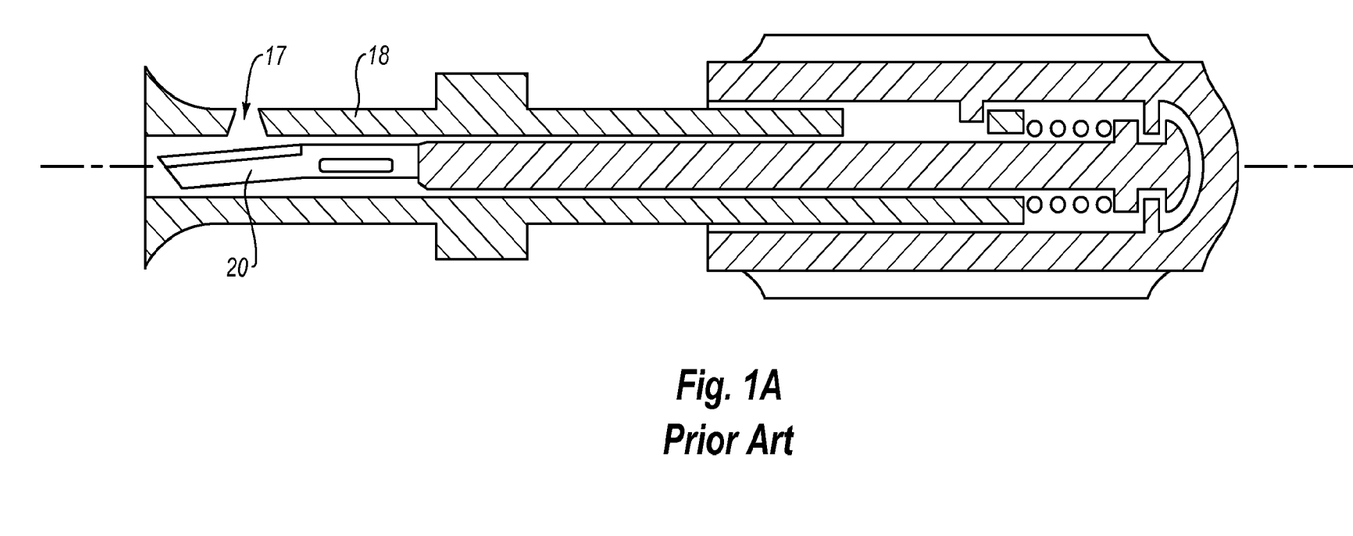
FIG. 1A is cross-sectional view through a prior art scalpel including a notch for cutting a suture.

Some efforts have been made to provide an ability to access the scalpel blade for cutting a suture while the blade is safely sheathed so as to prevent accidental cuts to the patient and/or practitoner. One such configuration is shown in U.S. Patent Application 2009/0157110, which includes a notch opening 17 in the side of the sheath 18 to allow a suture to be cut without exposing blade 20. As the suture is inserted into notch opening 17, tension between the suture and the blade 20 is used to cut the suture.

Figure 1B:
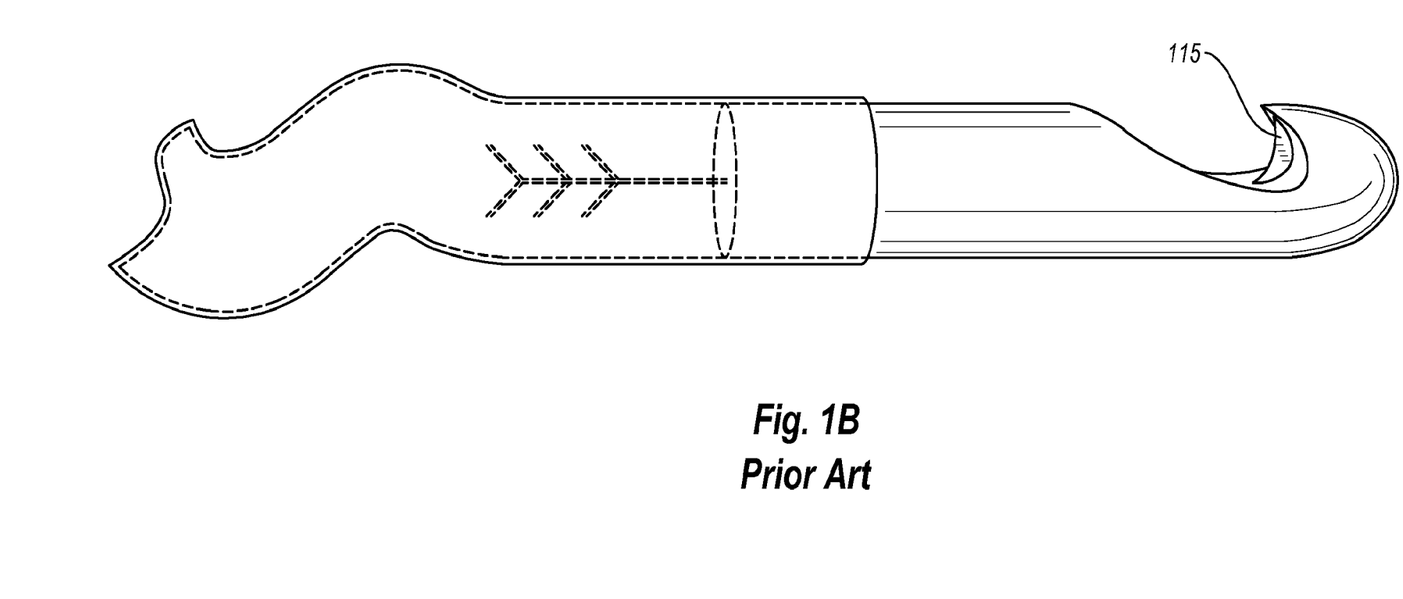
FIG. 1B is a perspective view of a prior art dedicated suture cutting device.

Another configuration is shown in FIG. 1B, which is taken from U.S. Patent Application 2005/0234481, and which discloses a dedicated suture cutting device in which the blade 115 is somewhat protected within an alcove at the distal end of the device. Similar to the device shown in FIG. 1A, the suture is pulled tight against the blade and tension between the blade and suture cuts the suture. Such a device is not capable of performing the traditional functions of a scalpel.

Although suture-cutting devices have been proposed, there still exists a need for improved configurations that effectively sheath the blade from accidental exposure, while providing easy, fast, and efficient cutting of a suture.

SUMMARY OF THE INVENTION

The present invention is directed to safety cutting devices, such as a scalpel that is manufactured In one embodiment, the device includes a sheath body configured to cover a scalpel blade at a distal end of a scalpel cutting device. The sheath body includes a suture guide slot formed into a surface of the body, and the slot extends from a first end at the edge of the sheath body to a second end adjacent the scalpel blade so that the slot intersects the blade, and the blade is exposed within the slot (i.e., at the second end or "bottom" of the slot), but is otherwise protected by the sheath. The slot includes a width defined by first and second opposed guiding side walls, and the blade is non-perpendicular relative to the slot. The angle between the first side wall of the slot and the scalpel blade at their point of intersection is advantageously greater than 105° and less than 180°.

In the case where the first and second side walls of the suture guide slot are parallel and the blade is straight, the angle between the second side wall and the blade at their point of intersection will be equal or approximately equal to 180° minus the angle between the first side wall and the blade at their point of intersection (i.e., the two angles can sum to 180°). Generally speaking, the side wall with the largest angle relative to the blade will have the shortest length, and vice-versa. In the case where the side walls are not parallel (e.g., they converge toward the blade) and/or the blade is not straight but curved, the sum of the two angles may not be 180°. Nevertheless, in general, when the first angle is obtuse (i.e., greater than 90°) the second angle will typically be acute (i.e., less than 90°).

In this embodiment, the slot walls and blade do not intersect one another in a substantially perpendicular configuration, but a more gradual angle of intersection is provided. This is advantageous as the cutting of the suture thus does not rely only on the tension between a suture that is perpendicular to the blade, and which is then pulled through the blade. Rather, the angle is significantly greater than 90° and the suture is pulled in a direction having a major component of motion that is parallel to the blade, while under slight tension, and with a minor component of motion that is perpendicular to the blade. This introduces a slicing action and allows the suture to be cut with considerably less force than is required when attempting to simply pull the suture through the blade where the orientation of the suture and blade are perpendicular relative to one another, and in which the applied force is largely perpendicular to the blade.

Such slicing or shearing action requires significantly less force to cut the suture because the component of motion or force that is perpendicular to the blade is reduced compared to when the angle is 90°. In other words, the suture motion has a significant component of motion that is parallel to the blade as the suture is pulled along the length of the blade within the slot. The interaction of the slot and suture causes the blade to progressively slice through the suture from the side, rather than there being no substantial movement of the suture along the blade length as is the case when the pulling or cutting force is perpendicular to the blade surface.

According to another embodiment, the device comprises a sheath body and a slot formed in the sheath body that intersects the scalpel blade so that the scalpel blade is exposed only within the slot, and in which the ratio of the length of the shortest slot side wall to the slot width is at least 2, more preferably at least about 3, and most preferably at least about 4. Such a ratio of slot depth to width is advantageous as it provides a greater safety factor to a user so as to keep the sharp blade well recessed and protected within the sheath compared to shallower a slot, and minimizes the tendency of the suture to be accidentally withdrawn from the slot as a result of inadvertently jerking or side-to-side movement of the suture. Such a ratio is independent of the suture diameter. For example, a larger diameter suture may benefit from a greater slot depth, as well as a greater slot width. When employed with a suture of typical diameter (e.g., about 0.1 to about 0.25 mm), the length of the shortest slot side wall may be at least 3 mm, more preferably at least about 4 mm, and more preferably at least about 5 mm from the first slot end at the edge of the sheath to where the slot intersects with the blade. In addition to better retaining the suture within the slot, such ratios and slot depths are particularly beneficial in keeping the sharp blade well away from the exterior end or side of the sheath so as to prevent accidental cuts.

The sheath may be separate and removable from the scalpel cutting tool, in which case the sheath is configured to be positioned over the distal blade end of the scalpel. In other embodiments, the sheath may be attached to the scalpel cutting tool so as to not be removable therefrom, but in which either the blade or sheath may be retracted, selectively exposing the blade.

An advantage of embodiments that include a suture guide slot at the forward end of a relatively narrow sheath is that the device can be maneuvered longitudinally to cut sutures in restricted spaces. The space in which such devices can cut may be limited only by the width of the sheath. This is in contrast to suture scissors, which often require much greater space to operate properly, or a suture cutting blade with the suture guide slot positioned on the side and that must be moved laterally (e.g., perpendicular to the longitudinal axis of the device) rather than longitudinally when cutting.

In some embodiments, the sheath may include spacing means for providing a desired blade height or distance from the skin or tissue surface. This can provide several desired functions, including leaving a suture end with a desired length and/or preventing inadvertent cutting of the suture knot, which should be positioned between the blade and the patient's tissue surface. An example of spacing means includes one or more rails or protrusions on a side of the sheath. The sheath can optionally include differently sized rails or protrusions on opposite sides of the sheath that maintain the cutting blade at different distances from the tissue surface to provide a practitioner with the ability to cut at different heights or distances from the skin depending on which side of the sheath is positioned next to the tissue surface.

In one embodiment the sheath includes a plurality of slots formed in the sheath. Such a configuration provides additional functionality and/or ease of manufacturing. For example, a single sheath configuration including a plurality of slots (e.g., two) may be manufactured so as to be used with scalpels including somewhat different blade configurations (e.g., which may require a slightly different slot location). Such a universal sheath allows a single sheath design to be used with multiple scalpels, easing manufacture and reducing costs. In addition, depending on the particular location of the slots and the configuration of the scalpel blade, the different slots may each intersect the scalpel blade and provide different characteristics for cutting a suture. For example, one slot may intersect the blade at a relatively shallow angle, providing the shearing benefits described herein, while another slot may intersect the blade at a less shallow angle nearer 90°, which may still be suitable for cutting relatively thin, low strength sutures.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. The drawings depict only typical embodiments of the invention and are not therefore to be considered limiting of its scope.

FIG. 2AA is a close up view of the slot and sheath of FIG. 2A;

FIG. 2BB is a close up view of the slot and sheath of FIG. 2B;

FIG. 3AA is a close up view of the slot and sheath of FIG. 3A;

FIG. 3AB is a close up view of the slot and sheath of FIG. 3A.

FIG. 3BB is a close up view of the slot and sheath of FIG. 3B;

DETAILED DESCRIPTION

I. Introduction

In one embodiment, the present invention is directed to a sheath for use with a scalpel cutting device including a sheath body configured to cover a scalpel blade at a distal end of a scalpel cutting device. The sheath advantageously includes a slot formed therein that extends from a first end at an edge of the sheath body to a second end adjacent the scalpel blade so that the slot intersects the blade and the blade is exposed only within the second end of the slot. The blade surface is non-perpendicular relative to the slot side walls, such that generally one side wall will be shorter than the other. The slot is further advantageously configured such that an angle between the first guiding side wall (e.g., the shorter side wall) of the slot and the scalpel blade at the point of intersection is greater than 105° and less than 180°. Where the slot side walls are parallel and the blade is straight, the angle between the second side wall and the blade at intersection will be supplementary to the first angle. Although the angles may not sum to 180° in embodiments including non-parallel slot side walls and/or curved blades, in general when the first angle is obtuse, the second angle will be acute.

In any case, the configuration advantageously allows a suture inserted within the slot to be sheared or sliced as the suture is pulled along the blade edge rather than simply pulled perpendicularly through the blade. Slicing the suture in this manner greatly decreases overall applied force, and particularly the component of the force applied in a direction perpendicular to the blade, which eases cutting of the suture, while also minimizing or preventing any tendency of the suture to tear through the patient's tissue as a result of the applied forces.

In another embodiment, the slot of the sheath is specifically configured to include a ratio of the length of the shortest slot side wall to the slot width that is at least 2. Such a ratio minimizes or prevents the tendency of the suture to accidentally become dislodged from the slot as a result of inadvertent movement. Such a ratio also provides sufficient slot depth to prevent accidental cuts caused by a blade which is disposed closer to the edge of the protective sheath. Even greater ratios of slot side wall length to slot width (e.g., at least about 3 or at least about 4) are even more effective at retaining the suture within the slot and preventing accidental cuts.

II. Exemplary Safety Suture Cutting Devices

Figure 2:
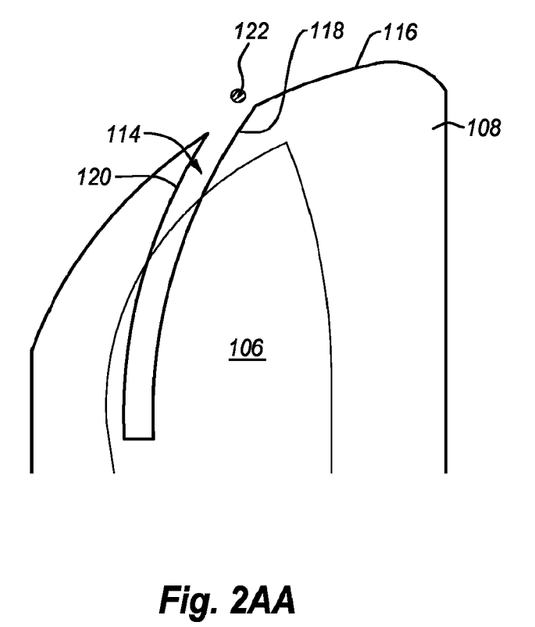
Figure 2A:
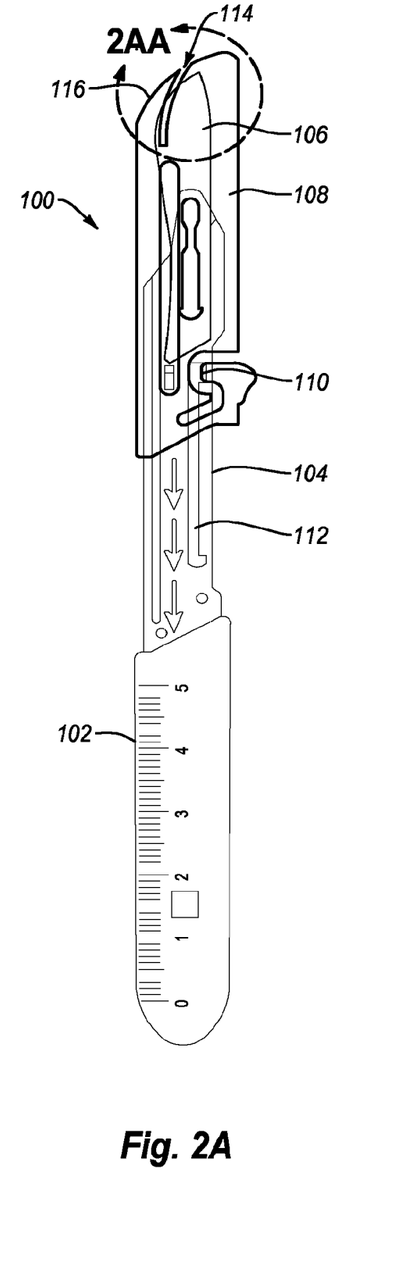
FIG. 2A is a front side view of an exemplary scalpel including a protective sheath having a slot formed in a distal end surface thereof according to the present invention.

FIG. 2A shows an exemplary scalpel 100 including a proximal gripping end 102 and a distal end 104 to which is attached a blade 106. A retractable sheath 108 is coupled over the distal end 104 so as to selectively cover and uncover blade 106. In the illustrated configuration, sheath 108 is fully extended, so as to fully cover blade 106. Retractable sheath 108 includes a tab 110 that rides within a guide slot 112 that allows the sheath to be selectively slid from the sheathed configuration shown to a configuration (not shown) in which blade 106 is exposed, extending through the distal end of sheath 108. Although one configuration of the retraction mechanism is shown, it will be understood that other retraction mechanisms may be employed. For example, in an alternative embodiment, it may be the blade that is retractable within a protective sheath (see FIGS. 3A-3B). In another embodiment, neither the sheath nor the blade may be retractable, but the sheath may be separate and removable from the scalpel. Such a removable sheath may simply be coupled or otherwise disposed over the blade so as to cover and protect the blade from accidental contact with another surface.

Figure 2B:
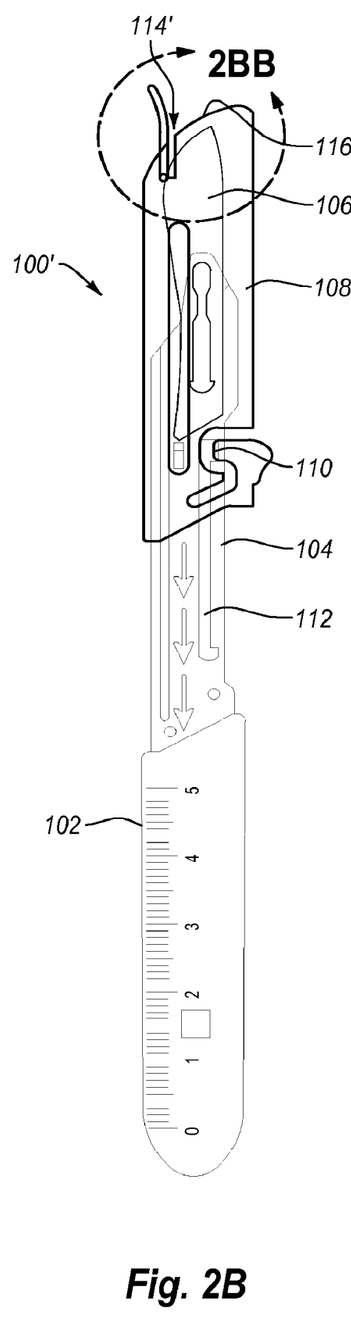
FIG. 2B is a front side view of an alternative scalpel including a protective sheath having a slot formed in a distal end surface thereof according to the present invention.

Sheath 108 includes a slot 114 formed therein. In the illustrated example, slot 114 extends from the distal end surface 116 of sheath 108 towards the sharp cutting surface of blade 106. Slot 114 intersects blade 106, as shown perhaps most clearly in FIG. 2AA. Slot 114 is shown in FIGS. 2A-2AA as being curved, while a straight slot is shown in FIGS. 2B-2BB. Slot 114 includes a first side wall 118 that acts as a guide surface on one side of slot 114 and a second side wall 120 that acts as another guide surface on the other side of slot 114. The width of the slot 114 is defined between side walls 118 and 120.

As seen in FIG. 2AA, a suture 122 can be introduced into slot 114 in preparation for easily and efficiently cutting the suture. For example, suture 122 may be guided downward along side wall 118 until it reaches the intersection of side wall 118 with blade 106. Because blade 106 advantageously forms an angle relative to side wall 118 that is greater than 90° and the slot 114 is sufficiently wide relative to the suture diameter, the suture 122 may be pulled across blade 106 towards opposite side wall 120, slicing through suture 122 with relatively little downward force applied. In other words, only a minor component of the applied force is directed perpendicular to the blade 106, while the major component or vector of the applied force is directed parallel to the blade 106. As a result of such a slicing action and configuration, the forces transmitted upwards through the suture to the patient's tissue are minimized. By comparison, when applying a force that is entirely (or nearly so) perpendicular to the blade without any substantial translation of the suture along the blade surface, not only is the magnitude of the component of the applied force that is perpendicular to the blade significantly greater, but the overall magnitude of the applied force must also be greater than that applied in the inventive embodiments. Such higher forces increase the tendency to tear the suture through the patient's flesh.

For example, before cutting, the opposite end of the suture may be stitched into the patient's tissue. As a result, it is desirable to minimize pulling forces on the suture that might otherwise pull the suture, cutting through the patient's tissue (e.g., similar to a cheese wire). The described configurations provide slot to blade angles and slot widths that are configured so as to minimize such tissue cutting forces. Preferably, the angle between the side wall 118 of the slot and the blade 106 is between about 130° and about 170°, more preferably between about 150° and about 170°. For example, the configuration shown in FIG. 2AA includes an angle of about 160° between side wall 118 and blade 106.

It will be appreciated that the angle formed between second side wall 120 of the slot and the blade will be supplementary to the above described angles where the side walls 118 and 120 are parallel and the blade is substantially straight within the slot 114. Although in embodiments including non-parallel side walls and/or blades exhibiting substantial curvature within the exposed portion of the slot the two angles may not sum to 180°, in general the angle associated with the shorter side wall will be obtuse, while the angle associated with the longer side wall will be acute.

The described configuration that introduces a slicing action when cutting the suture is particularly beneficial for use with strong, difficult to cut sutures. For example, some polymeric sutures are so strong that they are difficult if not impossible as a practical matter to cut by simply pulling the suture perpendicularly through a blade without tearing the just completed stitched portion of the suture through the patient's flesh. The particular slot to blade angle provided, as well as the blade length exposed within the slot selected may depend on the strength of sutures to be cut with the device. For example, stronger sutures may require a shallower angle (i.e., closer to 180°) and/or a greater ratio of exposed blade length to suture diameter. Relatively weaker sutures may be sliced without any cheese-wire effect of tearing through the patient's flesh with a sharper angle (i.e., closer to 105°) and/or a lower ratio of exposed blade length to suture diameter.

Figure 5A:
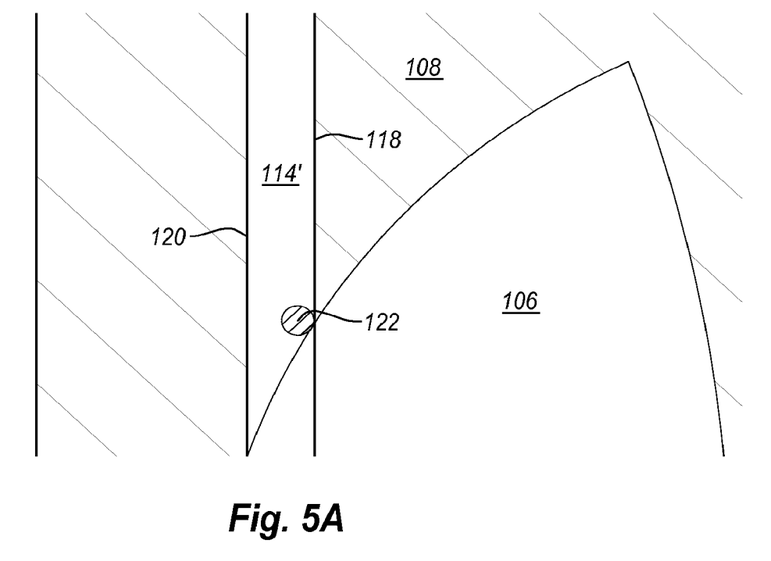
FIG. 5A is a partial cross-sectional view showing the distal end of a scalpel blade and sheath slot similar to that of FIG. 2BB in which a suture to be cut is positioned at the intersection of the slot and blade.
Figure 5B:
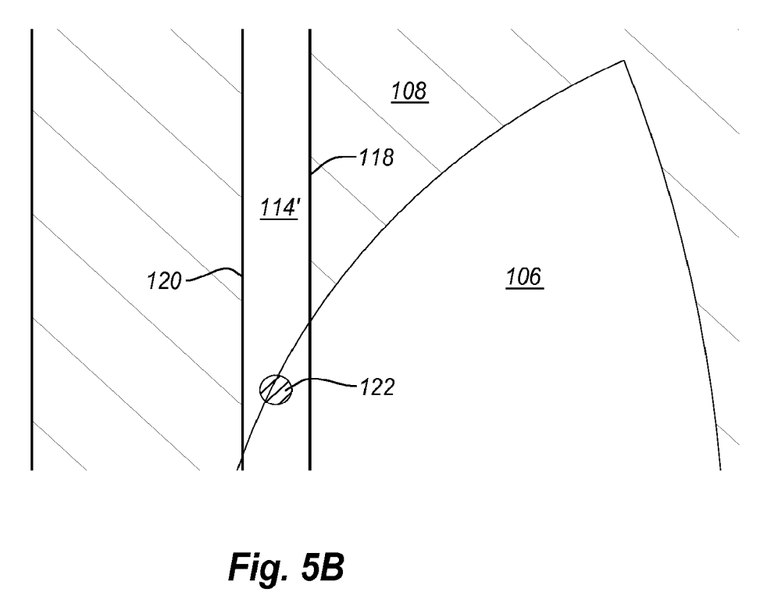
FIG. 5B is a partial cross-sectional view similar to that shown in FIG. 5A in which the suture has advanced along the exposed blade surface, slicing into the suture.

It is also noted that the width of slot 114 is significantly greater than the diameter or thickness of the suture 122 to be cut. The term "diameter" will be used hereinafter, although it will be understood that the suture may have a cross-section that is other than round, in which the diameter referred to is the suture thickness. This width of the slot 114 provides sufficient space for the suture to be pulled along the blade 106 while a small downward force component is applied so that the blade slices into the suture as it is pulled along blade 106. FIGS. 5A-5B, described in further detail below, show such a progressive slicing action. For example, the width of slot 114 may be such so as to provide a length of exposed blade 106 within slot 114 that is at least about 1.5 times the diameter of the suture 122 to be cut. In one embodiment, the exposed blade length within slot 114 may be at least about 2 times the suture diameter; in another embodiment the exposed blade length may be between about 4 times and about 12 times the suture diameter. For example, the arc length of blade 106 illustrated in FIG. 2AA is about 6 times the diameter of suture 122. The width of slot 114 should not be so great as to allow inadvertent cutting of a practitioner's finger or other appendage.

FIGS. 2B-2BB illustrate another embodiment of a scalpel 100' that is similar to that shown in FIGS. 2A-2AA, but in which the slot 114' is substantially straight rather than curved. In addition, scalpel 100' further includes a guide member 124 disposed adjacent slot 114' that extends beyond the distal mouth of slot 114', adjacent sidewall 120 so as to aid in guiding suture 122 into slot 114'. Such a guide member is beneficial in helping to introduce the suture into slot 114' (e.g., by placing suture 122 in contact with guide 124 and then pulling suture 122 downward, where it is guided into slot 114'). Guide member 124 may alternatively be positioned adjacent guiding side wall 118. Such a guide member may be provided with any of the embodiments described herein.

In addition, the mouth of slot 114' is shown as being flared in embodiment 100', while that of FIGS. 2A-2AA is not flared. Although both slots 114 and 114' are shown as having a substantially constant width over substantially the entire depth of the slot, it will be understood that alternative embodiments may include non-parallel side walls so that the width varies. For example, one embodiment may include side walls that converge towards the blade, which facilitates easier introduction of the suture into the slot. In another example, an embodiment may include a mouth of a given width, which widens as the slot approaches the blade 106. Such a configuration may be beneficial in helping to prevent accidental release of the suture 122 after entrance into the slot, while also providing the desired ratio of exposed blade length to suture diameter where the slicing occurs (i.e., at the blade edge). Where the width of the slot varies, the sidewalls may be smooth or may include an abrupt transition, as desired.

Figure 3:
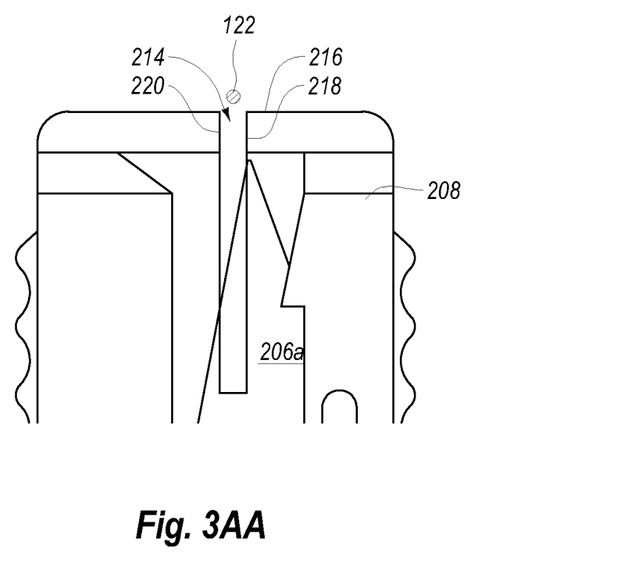
Figures 3, 3B, 4A, 4B:
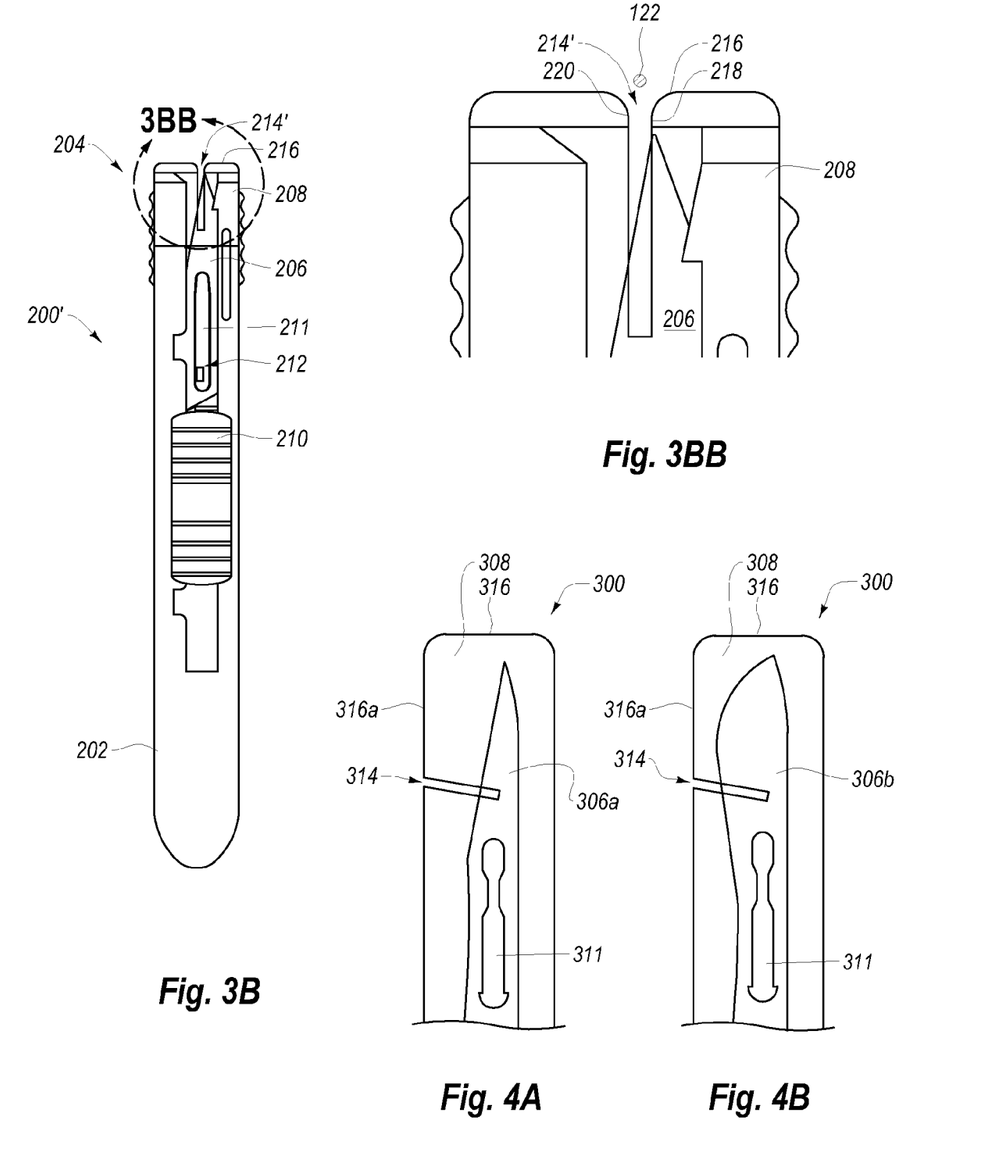
FIG. 3B is a front side view of another scalpel including a protective sheath having a slot formed in a distal end surface thereof according to the present invention.
FIG. 4A is a front side view of the distal end of another scalpel including a protective sheath having a slot formed in a side surface thereof according to another embodiment of the present invention.
FIG. 4B is a front side view of the distal end of another scalpel including a protective sheath having a slot formed in a side surface thereof.
Figure 3A:
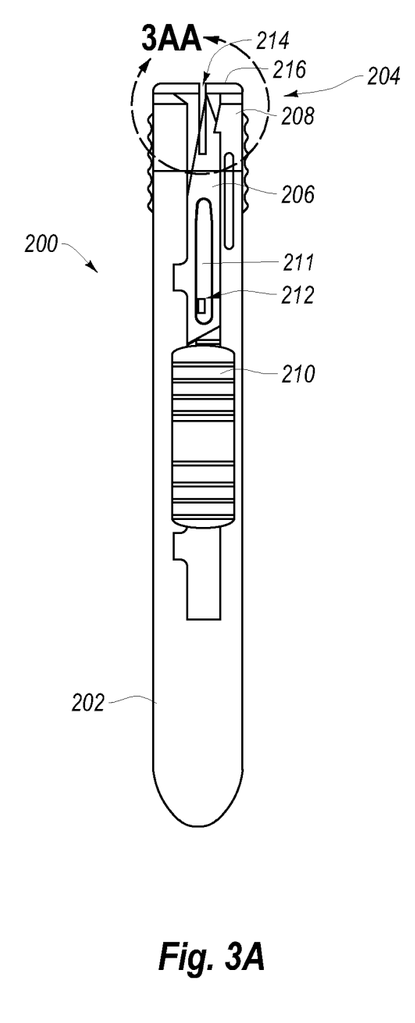
FIG. 3A is a front side view of another scalpel including a protective sheath having a slot formed in a distal end surface thereof according to the present invention.

FIGS. 3A, 3AA, and 3AB illustrate another embodiment of a scalpel 200 including a proximal gripping end 202 and a distal end 204 within which is disposed a blade 206a (206b in FIG. 3AB). In this embodiment, it is the blade 206a or 206b that is extendable beyond and retractable within the distal end 204 of the scalpel 200. Distal end 204 includes a sheath 208 within which blade 206a or 206b may be selectively retracted and protected. Retractable blade 206a or 206b may be attached to a slidable member 210 that rides within a guiding slot 212 that allows the blade 206a or 206b to be selectively slid from the sheathed configuration (shown) to a configuration in which blade 206a or 206b extends beyond distal end 216 of sheath 208. It will be understood that other retraction mechanisms may be employed, or that the sheath may be separate and removable from the scalpel cutting tool. FIG. 3AA shows blade 206a as an 11 blade. FIG. 3AB is substantially similar to FIG. 3AA except blade 206b is a 10 blade.

Similar to the above described embodiments, sheath 208 includes a slot 214 formed therein. In the illustrated example, slot 214 extends from the distal end surface 216 of sheath 208 towards blade 206a or 206b. Slot 214 intersects blade 206a or 206b, as shown perhaps most clearly in FIG. 3AA or FIG. 3AB. Slot 214 is shown in FIGS. 3A, 3AA, and 3AB as being substantially straight and vertical (i.e., parallel to a longitudinal axis of the scalpel 200), rather than curved as shown in FIGS. 2A-2AA. Slot 214 includes a first side wall 218 that acts as a guide surface on one side of slot 214 and a parallel second side wall 220 that acts as another guide surface on the opposite side of slot 214. The width of the slot 214 is defined between side walls 218 and 220. Another difference of scalpel 200 in FIGS. 3A and 3AA is that blade 206 is shown as having a substantially straight cutting edge, rather than the curved cutting edge shown in FIGS. 2A-2BB and FIG. 3AB. In addition, the distal end 216 of sheath 208 is illustrated as flat (i.e., perpendicular to a longitudinal axis of the scalpel), rather than including a curved distal end surface as the embodiments of FIGS. 2A-2BB. It will be understood that various sheath and blade configurations may be used within any given embodiment. For example, one embodiment (not shown) may include a straight edged blade as in FIG. 3A-3BB with a curved end sheath as in FIG. 2A-2BB.

FIGS. 3B-3BB illustrate another embodiment of a scalpel 200' similar to that of FIG. 3A-3AA, but in which the mouth of slot 214' is flared rather than square, as is the mouth of slot 214. Flaring may aid a user in introducing the suture 122 into the slot.

Table I below shows shorter side wall to blade edge angle information (Angle), exposed blade length to suture diameter ratios (Ratio 1), and shorter side wall length to slot width ratios (Ratio 2) for the embodiments shown in FIGS. 2AA, 2BB, 3AA, 3BB, and FIGS. 4A and 4B.

TABLE I

| Example | Angle | Ratio 1 | Ratio 2 |
|---|---|---|---|
| FIG. 2AA | 158° | 6.1 | 3.8 |
| FIG. 2BB | 149° | 4.8 | 2.9 |
| FIG. 3AA | 169° | 10.9 | 2.4 |
| FIG. 3BB | 169° | 10.9 | 2.4 |
| FIG. 4A | 90° | 2.0 | 6.5 |

FIGS. 4A and 4B illustrate another alternative embodiment. As will be readily appreciated, in this embodiment, both the side walls of slot 314 form an angle relative to blade 306a (FIG. 4A) that is less than 105° (e.g., about 90° for each), and the slot 314 is formed into a lateral side 316a, rather than the distal end 316 of sheath 308. As such, this embodiment may be less preferred for reasons described above relative to the preferred angles that are greater than 90° and the associated slicing action achieved, but this embodiment illustrates other desirable features that may be incorporated into the inventive devices. FIG. 4A shows blade 306a as an 11 blade attached to connector 311. FIG. 4B shows blade 306b as a 10 blade attached to connector 311.

For example, scalpel 300 includes a slot 314 having a ratio of the length of the shortest side wall of slot 314 to slot width that is at least 2, more preferably at least about 3. In some embodiments, the ratio may be even greater (e.g., at least about 4). Such a ratio is independent of the suture diameter to be cut. Such a configuration provides an additional degree of safety over the prior art embodiment shown in FIG. 1A, in which the slot appears wide and short rather than exhibiting the greater ratios herein described. In such embodiments, the higher ratio of side wall length to slot width aids in retaining the suture within the slot 314 once introduced. With a shallower slot, the suture may easily become dislodged from the slot, leading to frustration and wasting the time of the practitioner. In addition, shallow and wide slots may position the blade dangerously close to the notch formed in the side of the sheath.

When used with typically sized sutures (e.g., about 0.1 mm to about 0.25 mm in diameter), the length of the shortest side wall may be at least 3 mm, more preferably at least about 4 mm, and even more preferably at least about 5 mm. Even greater lengths are possible (e.g., 8 mm or 10 mm). Of course, ratios of shortest side wall to slot width of at least 2, at least 3, at least 4 and slot depths of at least 3 mm, 4 mm, 5 mm or more as described above may be included within the embodiments illustrated and described above in conjunction with FIGS. 2A-3BB, which configurations may be particularly preferred as providing collectively the most benefits. In addition, the slots of any of the embodiments shown in FIGS. 2A-3BB may be formed into a lateral side, rather than the distal end of the sheath.

FIG. 5A illustrates a further close up view similar to the scalpel embodiment shown in FIG. 2BB, in which the suture 122 is positioned at the intersection of guiding side wall 118 and blade 106. As shown in FIG. 5B, as the suture is pulled along the edge of blade 106, blade 106 slices into the side of suture 122. The applied force includes a minor component that is in a direction perpendicular to the blade surface and a major component that is in a direction parallel to the blade surface. For example, as seen in FIG. 5B the suture 122 has advanced about half way along the length of the exposed blade edge, slicing nearly completely through suture 122. Suture 122 will be completely severed prior to reaching opposite guiding side wall 120. Of course, the device may be used by initially positioning the suture 122 at the intersection of side wall 120 and blade 106 and advancing along blade 106 in the opposite direction, although it may be preferred to progress "down" the blade 106, rather than "up" the blade 106.

Each of the described embodiments advantageously provides the ability to safely and efficiently cut a suture without having to extend the scalpel blade to an unprotected position in order to perform the cutting.

Figure 6:
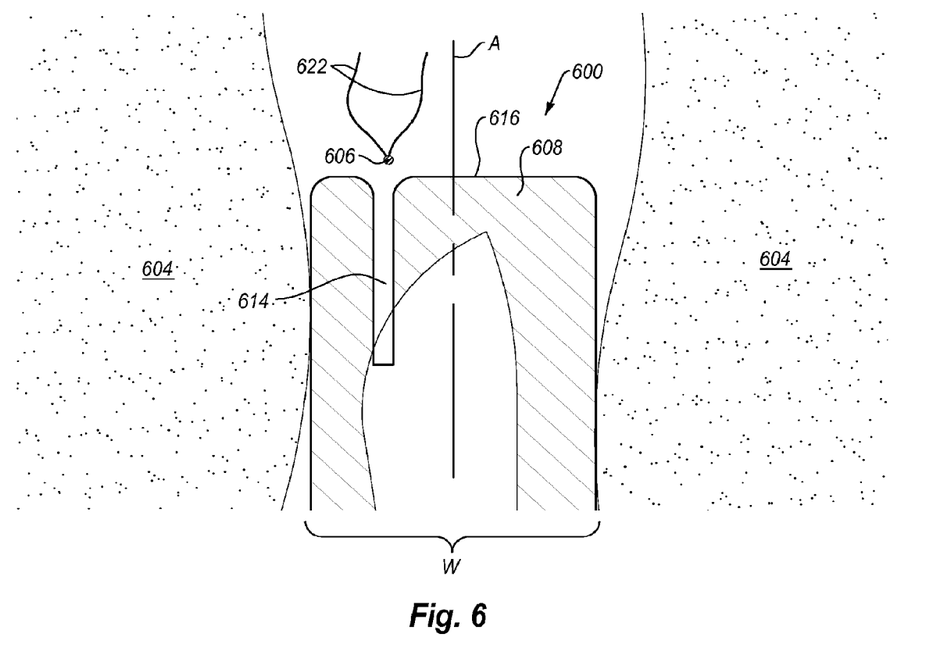
FIG. 6 illustrates how an exemplary safety suture cutting device is able to cut a suture in a restricted space.

As illustrated in FIG. 6, an advantage of embodiments that include a suture guide slot 614 at the forward end 616 of a relatively narrow sheath 608 is that the device 600 can be maneuvered longitudinally (i.e., in a direction that is generally parallel to the longitudinal axis A of the device) to cut sutures 622 in a restricted space defined by obstructions 604 on one or both sides of the suture knot 606. The space in which such devices can cut may be limited only by the width W of the sheath 608. This is in contrast to suture scissors, which often require much greater space to operate properly, or a suture cutting blade with the suture guide slot positioned on the side and that must be moved laterally (e.g., perpendicular to the longitudinal axis A of the device) rather than longitudinally when cutting. The width W can be configured to be about 1 inch (about 25 mm) or less, for example, not more than about 0.5 inch so as to allow the device to slide easily between closely spaced obstacles, cutting a suture disposed therebetween. For example, with scissors, if the practitioner were required to open the scissor blades to more than width W, then the convenience and/or effectiveness of the cutting is negatively affected. With a device including a suture guide slot positioned on the side, the practitioner may be required to orient the device and blade so as to face the patient's tissue, which can result inadvertent cuts to the patient.

III. Safety Scalpels and Methods for Manufacturing Safety Scalpels with Different Sized Blades One embodiment of the invention relates to methods for manufacturing copies of a scalpel with different sized blades using the same molded scalpel parts. The scalpels are manufactured using the same housing or sheath and/or the same support member for the blade. support structure for the blades minimizes the cost of manufacturing, assembly, and FDA approval.

The method can include all or a portion of the following steps: (i) providing a plurality of copies of a first sized scalpel blade and a plurality of copies of a second sized scalpel blade, the first sized scalpel blade having a differently shaped cutting edge than the second sized scalpel blade; (ii) injection molding a plurality of copies of a safety scalpel support structure, the support structure having a connector that receives the first and second sized scalpel blades; (iii) injection molding a plurality of copies of a safety scalpel sheath, the safety scalpel sheath configured to be operably coupled to the support structure to move between a safe position and a cutting position, the sheath having a size and shape that accommodates the first sized scalpel blade and the second sized scalpel blade individually when positioned therein (i.e., the sheath can separately accommodates both the blades, but not necessarily both at the same time); (iv) the sheath having a transverse slot that (1) intersects the cutting edge of the first sized scalpel blade when assembled therewith in the safe position and (2) intersects the cutting edge of the second sized scalpel blades when assembled therewith in the safe position; (v) optionally injection molding a plurality of copies of one or more additional scalpel components; (vi) assembling a plurality of copies of safety scalpels, where a first portion of the copies of safety scalpels are each assembled from one copy of the first scalpel blade, one copy of the sheath, one copy of the support structure, and optionally one copy of the one or more additional scalpel components; and a second portion of the copies of scalpels are each assembled from one copy of the second sized scalpel blade, one copy of the sheath, one copy of the support structure, and optionally one copy of the one or more additional scalpel components, thereby forming the plurality of safety scalpels with different sized blades that have a slot for cutting suture.

The use of the same injection molded parts for assembling the different copies of the scalpel ensures a familiarity between different scalpels while still accommodating different blade shapes and providing a suture trimming groove (i.e., the transverse slot). This feature can be highly valuable for encouraging physicians to use the safety features. Familiarity is important to adoption. The literature has shown that the safety features on existing devices are frequently not used, which has hindered the ability to protect clinicians and patients from accidental sharps injuries. Thus, providing an intuitive way to activate the safety feature and ensuring familiarity between devices with different sized blades (while still providing a transverse slot) can overcome the problems with existing device (i.e., the lack of user adoption).

The sheath and/or the support structure are typically formed from a polymerizable material that is injected into the mold and allowed to cure for a sufficient period of time to allow the part to be removed from the mold with the desired form. Those skilled in the art are familiar with suitable polymerizable materials and the techniques for forming molds into which the polymerizable material may be injected. In some embodiments the sheath and the support structure are injection molded from the same mold. The mold may be a steel mold or an aluminum mold. The mold may be multi-cavity and the multi-cavities may include a plurality of copies of the same part.

In some embodiments, the injection-molded parts may be made from a color that is coordinated with a particular blade type. For example the support structure may be made from a different colored plastic when injection molding a support structure that fits a 10 blade verses an 11 blade. For example, the support structure may be a particular color for a 10 blade and a particular different color for the 11 blade. The color coordinated scalpel part may be the support structure the sheath and/or any other components of the scalpel device.

In some embodiments the first and second sized scalpel blades have a same blade connector for attachment to the support structure. Using the same blade connector allows different blade to be connected directly to the same support structure. Since the blades are of different shapes, the transverse slot needs to be carefully selected to ensure that it transects the cutting edge of both blades in the different scalpel copies.

In some embodiments, the scalpel blade may have a straight cutting edge or a curved cutting edge and in some embodiments a portion of the copies of the scalpel have a straight cutting edge and a portion have a rounded cutting edge. The blade may be a scalpel blade sized according to the standard blades used with a Bard Parker type handle. In this embodiment, a 10 blade is a rounded blade commonly used to cut skin and an 11 blade is a straight blade commonly used to piece the skin. The 15 blade is a rounded blade that is much smaller than the 10 blade and is used for fine articulation of the blade (e.g., mole removal). The blade may have a cutting edge (i.e., sharpened portion) that is at least 10 mm, 12.5 mm, or 15 mm long and/or less than 30 mm, 25 mm, 20 mm or within a range thereof.

In some embodiments, the method can include providing a third sized scalpel blade and wherein the transverse slot is configured to intersect the thirds sized scalpel blade when assembled therewith in the safe position. In some embodiments the copies of scalpel devices include three size of scalpel blades that can be used to trim suture in the transverse slot when assembled and the sheath is in the safe position. The three sized scalpel blades may be a 10 blade, an 11, blade, and a 15 blade.

In some embodiments the number of copies of assembled scalpel devices from the same mold design is greater than 100,000, 1 million, or 10 million.

In some embodiments the length of the slot can have a length suitable for accommodating a variety of different scalpel cutting edges. The slot may have a length of greater than 4, 6, 8, 10 mm and less than 30, 25, 20, 15, mm or within a range thereof. The median width of the slot may be greater than or equal to 0.75 mm, 1.0 mm, 1.25 mm and/or less than or equal to 3 mm, 2.0 mm, or 1.5 mm, or within a range thereof. Slot may also have a ratio of slot length by average width of greater than 1, 1.5, 2, 2.5, or 3 and/or less than 10, 7, 5, or 3 or within a range thereof.

The slot may intersect the cutting edges of the first and the second sized blades and/or a third sized blade at an angle greater than or equal to 105, 115, 125, 135, 145, 150 degrees and/or less than 180, 170, or 160. For slots that intersect a non-linear blade the angle may be calculated from the intersection of the most obtuse angle (i.e., the location where a suture would eventually reach when sliding therethrough).

The angle of the slot may also be selected to be somewhat parallel to the axis of the device, which is advantageous for manipulating the device in tight spaces. In some embodiments, the transverse slot extends into the sheath at an angle less 70, 65, 60, 55, 45, 40, 35, 30, 25, 20, 15, 10, 5 degrees relative to a longitudinal axis of the safety scalpel. For a slot that is not curved, the axis of the slot is the average angle of the sidewall of the slot. In some embodiments the transverse slot extends into the sheath from an anterior end of the safety scalpel. In other embodiments, the transverse slot may extend in from a lateral edge of the safety scalpel.

In some embodiments, the sheath can have rigid sidewalls that form the transverse slots to minimize the flex or play in the sidewall as the suture travels through the slot. This feature ensures that pressure from the suture does not cause the sidewall to flex or breakaway, thereby inhibiting the suture from being cut or increasing the possibility that the suture will be captured between the sidewall and the blade and then cause tugging or pulling on the skin just before the suture breaks. For purposes of this invention a sidewall that is rigid is sufficiently rigid so as to not break away for replacing the blade. An example of a "non-rigid" sidewall of a sheath is illustrated in U.S. Pat. No. 8,181,352 to Shackelford.

The present invention also extends to the scalpels manufactured by the methods described herein. The scalpels manufactured according to the methods are unique as compared to scalpels manufactured using other techniques because they provide a suture cutting groove on scalpels with different sized blade, yet provide a familiarity between the different scalpels. The familiarity between scalpels is important for encouraging proper behavior amongst physicians. Physicians that learn to use a safety scalpel with one sized blade are more likely to activate the safety feature of a different sized blade that he or she uses less frequently if the look and feel of the scalpel is otherwise the same. The present invention accomplishes this feat with a transverse slot (i.e., the suture cutting groove) for two or more different sized bladed. The suture cutting groove is usable with the sheath in the closed or protected position, thereby encouraging physicians to place the blade in the safe position in order to use the suture trimming feature.

Additional examples of scalpel cutting devices that can be manufactured according to the present invention are disclosed in Applicant's U.S. Provisional Application No. 61/733,433 filed Dec. 5, 2012, and in U.S. Pat. No. 8,465, 512, issued Jun. 18, 2013, which are hereby incorporated by reference in their entireties. The '433 application illustrates a scalpel device where the support structure is a slider and the sheath is formed by two housing pieces. The slider and the two housing pieces may be manufactured according to the method described herein.

The devices and methods described in Applicant's '433 application can include any of the features described in this application. For example, the devices of the '433 application may include the blade sizes described herein and the features of the transverse slot described herein. In addition the scalpel device of the '433 may have additional features such as a slider that is rigid in the area that supports the blade and has a thinned out portion in an anterior portion to allow the slider to flex during assembly. For example, the slider may have a bendable portion where the thickness of the material in the direction tangential to the bend is less than or equal to 4 mm, 3 mm, 2.5 mm, or 2 mm and/or greater than or equal to 1.0 mm, 1.5 mm, 2.0 mm, or within a range thereof. The housing forming a sheath may also have increased rigidity by having a spine of interlocking protrusions. In some embodiments all or a portion of the interlocking protrusions can include snap connect protrusions to facilitate simple assembly of a two-part housing.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope. Additionally, as used in this specification and the appended claims, the singular forms "a," "an" and "the" include plural referents unless the context clearly dictates otherwise.

Any of the foregoing embodiments described above may be used alone or in combination with one another and/or the embodiments disclosed in the references incorporated herein by reference.

I claim:

1. A set of safety scalpel devices, comprising:
a first subset of the safety scalpels having a first sized scalpel blade and a second subset of the safety scalpels having a second sized scalpel blade, the first sized scalpel blade having a differently shaped cutting edge than the second sized scalpel blade, wherein each of the subsets of safety scalpels includes:
an identical safety scalpel support structure, the support structure having a connector that receives the first and second sized scalpel blades, individually;
a safety scalpel sheath configured to be operably coupled to the support structure to move relative to a respective one of the scalpel blades between a safe position in which the respective one of the scalpel blades is covered by the sheath and an exposed position in which the respective one of the scalpel blades is exposed for cutting tissue, the sheath having a size and shape that accommodates the first sized scalpel blade and the second sized scalpel blade, individually;
the sheath having a transverse slot suitable for cutting suture, wherein the slot (i) intersects the cutting edge of the first sized scalpel blade when the sheath is assembled therewith and the first sized blade is in the safe position and (ii) intersects the cutting edge of the second sized scalpel blade when the sheath is assembled therewith and the second sized blade is in the safe position.

2. The set of safety devices as in claim 1, wherein the safety scalpel sheaths are injection molded parts.

3. The set of safety devices as in claim 1, wherein the support structures are injection molded parts.

4. The set of safety devices as in claim 1, wherein the first sized scalpel blade is an 11 blade and the second sized scalpel blade is a 10 blade or a 15 blade.

5. The set of safety devices as in claim 1 further comprising a third subset of safety scalpels having a third sized scalpel blade, a third support structure, a third sheath with a third transverse slot that is operably coupled to the third support structure to move thereby defining the safe and exposed positions of the third sized scalpel blade, wherein the third transverse slot is configured to intersect the third sized scalpel blade when the third sized scalpel blade is in the safe position.

6. The set of safety devices as in claim 5, wherein the first, second, and third sized scalpel blades are a 10 blade, an 11, blade, and a 15 blade of the first, second, and third subsets, respectively.

7. The set of safety devices as in claim 1, wherein the slot of any one of the subsets of safety scalpels has a length in a range from 4 mm to 30 mm.

8. The set of safety devices as in claim 1, wherein the slot of any one of the subsets of safety scalpels has a ratio of a length and an opening width of greater than 2.

9. The set of safety devices as in claim 1, wherein the slot of any one of the subsets of safety scalpels intersects the cutting edges of the first and the second sized blades at an angle greater than or equal to 105 degrees.

10. The set of safety devices as in claim 1, wherein the transverse slot extends into the sheath at an angle less than 70 degrees relative to a longitudinal axis of any one of the subsets of safety scalpels.

11. The set of safety devices as in claim 1, wherein the transverse slot extends into the sheath from an anterior end of any one of the subsets of safety scalpels.

12. The set of safety devices as in claim 1, wherein the transverse slot extends into the sheath from a lateral edge of any one of the subsets of safety scalpels.

13. The set of safety devices as in claim 1, wherein the sheath and the support structure for any one of the subsets of safety scalpels are injection molded parts.

14. The set of safety devices as in claim 1, wherein the first and second sized scalpel blades have identical blade connectors that are received by the connector of the support structure.

* * * * *